(12) United States Patent
Iwamoto (10) Patent No.: US 9,372,209 B2
(45) Date of Patent: Jun. 21, 2016

(54) SENSOR FOR DETECTING DAMAGE TO AN OBJECT (75) Inventor: Takashi Iwamoto, Chiba (JP)

(73) Assignee: Empire Technology Development LLC, Wilmington, DE (US)

( * ) Notice: Subject to any disclaimer, the term of this patent is extended or adjusted under 35 U.S.C. 154(b) by 299 days.

(21) Appl. No.: 13/641,242

(22) PCT Filed: Apr. 24, 2012

(86) PCT No.: PCT/JP2012/002805
§ 371 (c)(1),
(2), (4) Date: Oct. 15, 2012

(87) PCT Pub. No.: WO2013/160936
PCT Pub. Date: Oct. 31, 2013

(65) Prior Publication Data
US 2013/0278275 A1    Oct. 24, 2013

(51) Int. Cl.
G01R 27/04    (2006.01)
G01R 19/00    (2006.01)
G01R 3/00     (2006.01)
G01N 17/04    (2006.01)

(52) U.S. Cl.
CPC ............... *G01R 19/00* (2013.01); *G01N 17/04* (2013.01); *G01R 3/00* (2013.01); *Y10T 29/49117* (2015.01)

(58) Field of Classification Search
CPC ........ G01N 27/00–27/26; G01N 17/00–17/04; G01N 22/00; G01N 22/04; G01R 27/32
USPC .................................................. 324/637, 629
See application file for complete search history.

(56) References Cited

U.S. PATENT DOCUMENTS

| | | | | |
|---|---|---|---|---|
| 3,863,250 A | * | 1/1975 | McCluskey, Jr. | 340/550 |
| 3,922,629 A | * | 11/1975 | Hayakawa | 367/13 |
| 4,072,936 A | * | 2/1978 | Spirig | 340/566 |
| 4,689,552 A | * | 8/1987 | Fujii et al. | 324/546 |
| 4,752,360 A | | 6/1988 | Jasinski | |
| 4,784,729 A | | 11/1988 | Jasinski | |
| 4,840,719 A | | 6/1989 | Jasinski | |
| 4,863,572 A | | 9/1989 | Jasinski | |

(Continued)

FOREIGN PATENT DOCUMENTS

| CN | 101504384 A | 8/2009 |
|---|---|---|
| CN | 102112862 A | 6/2011 |

(Continued)

OTHER PUBLICATIONS

International Search Report and Written Opinion for PCT/JP2012/002805 dated Jul. 31, 2012.

(Continued)

*Primary Examiner* — Tung X Nguyen
*Assistant Examiner* — Dominic Hawkins
(74) *Attorney, Agent, or Firm* — Pepper Hamilton LLP (57) ABSTRACT A sensor for detecting damage to an object may include a housing, a first coating provided on a surface of a first end of the housing, and a second coating provided on a surface of a second end of the housing opposing the first end. The first coating may be configured to be exposed to an environment in which the object is placed, while the second coating may be configured to be hermetically sealed. The sensor may further include a plurality of electrodes placed in the housing connected to the first end and the second end so as to measure an electrical signal generated therebetween.

26 Claims, 6 Drawing Sheets

(56) References Cited

U.S. PATENT DOCUMENTS

| | | | |
|---|---|---|---|
| 5,089,695 A * | 2/1992 | Willson et al. | 250/227.21 |
| 5,734,323 A | 3/1998 | Hermes et al. | |
| 5,830,339 A * | 11/1998 | Watanabe et al. | 204/426 |
| 7,504,992 B2 * | 3/2009 | Pilcher et al. | 342/125 |
| 7,928,394 B1 * | 4/2011 | Richer | 250/343 |
| 2007/0114365 A1 * | 5/2007 | Potyrailo et al. | 250/221 |
| 2007/0144272 A1 * | 6/2007 | Yu et al. | 73/862.046 |
| 2007/0284966 A1 * | 12/2007 | Kadota et al. | 310/313 R |
| 2009/0033545 A1 * | 2/2009 | Pilcher et al. | 342/125 |
| 2009/0193872 A1 * | 8/2009 | Tokuda et al. | 73/23.31 |
| 2010/0007325 A1 * | 1/2010 | Stark | 324/71.1 |
| 2010/0030519 A1 * | 2/2010 | Collier et al. | 702/181 |
| 2010/0052704 A1 | 3/2010 | Fay et al. | |
| 2010/0090802 A1 * | 4/2010 | Nilsson et al. | 340/10.1 |
| 2011/0137142 A1 * | 6/2011 | Lucisano et al. | 600/347 |
| 2012/0134003 A1 * | 5/2012 | Yeh et al. | 359/265 |
| 2012/0188078 A1 * | 7/2012 | Soles et al. | 340/540 |
| 2012/0292759 A1 * | 11/2012 | Ishikawa | 257/737 |
| 2012/0318925 A1 * | 12/2012 | Gibson et al. | 244/158.3 |

FOREIGN PATENT DOCUMENTS

| | | |
|---|---|---|
| CN | 102149954 A | 8/2011 |
| EP | 0174768 A2 | 3/1986 |
| EP | 0258170 A2 | 3/1988 |
| EP | 2366099 A1 | 9/2011 |
| JP | 63-132154 A | 6/1988 |
| JP | 2002-039810 | 2/2002 |
| JP | 2010-237090 | 10/2010 |
| JP | 2012-018018 | 1/2012 |
| JP | 2012-501461 | 1/2012 |
| WO | WO2010/028035 A1 | 3/2010 |

OTHER PUBLICATIONS

Guran et al., Structronic Systems: Smart Structures, Devices and Systems: Materials and Structures (Series on Stability, Vibration and Control of Systems. Series, World Science Pub. Co. Inc. (Sep. 1998), http://bookweb.kinkokuniya.co.jp/htmy/9810229550.html.

Kataoka et al., Ionic Conduction Mechanism of PEO-Type Polymer Electrolytes Investigated by the Carrier Diffusion Phenomenon Using PGSE-NMR, *Macromolecules* (Jul. 9, 2002), 36(16):6239-6244 (Abstract).

Macomber et al., Chemical Sensing Through Measurement of Thickness/Impedance Characteristics of Ion-Conducting Polymer Films, *J. Electrochem. Soc.* (Jun. 16, 2003), 150(8):H172-H177 (Abstract).

Mannoor et al., Electrical detection of pathogenic bacteria via immobilized antimicrobial peptides, *Proceedings of the National Academy of Sciences* (Oct. 18, 2010), 107(45):19207-19212.

Masahiro et al., Ion transfer at interface between lithium ion conductive electrolytes, *Extended Abstracts, Symposium on Solid State Ionics in Japan* (2001), 27:14-15 (Abstract).

Morita et al., Crack Detection Methods Using Radio Frequency Identification and Electrically Conductive Materials, *Technical Memorandum of Public Works Research Institute* (2006), 4022:88.

Sensor Paints herald new era of responsive materials, http://www.nanowerk.com/spotlight/spotid=7453.php (Sep. 26, 2008).

Yang et al., Electrical/electrochemical impedance for rapid detection of foodborne pathogenic bacteria, *Biotechnology Advances* (Nov. 12, 2007), 26:135-150.

Yoon et al., Passive wireless sensors using electrical transition of carbon nanotube junctions in polymer matrix, *Smart Mater. Struct.* (Dec. 13, 2005), 15:S14-S20.

Aldraihema et al., Nanocomposite functional paint sensor for vibration and noise monitoring, *Sensors and Actuators A: Physical* (Nov. 27, 2008), 149(2):233-240.

Kim et al., Ion Conductivity of Polymer Electrolytes Based on PEO Containing Li Salt and Additive Salt, *Solid State Phenomena* (Jan. 15, 2007), 119:119-122.

RFID 125 KHz EM4100 Screw Tag, retrieved from URL: http://www.alibaba.com/product-detail/RFID-125-KHz-EM4100-Screw-Tag__265769775.html, on Jan. 23, 2014, p. 1-2.

SH698 Screw RFID Tag Specification, retrieved from URL: http://smarthomeuae.com/new3/product.php?productid=698&pcategory=15005, on Jan. 23, 2015, p. 1-2.

Hua-Ming et al., Study on Electrical and Thermal Properties of PMMA/Aligned Carbon Nanotubes Composites, *Chinese Journal of Inorganic Chemistry* (Sep. 2005), 21(9):1353-1357.

Search report for Chinese counterpart application No. CN 2012800725700.

\* cited by examiner

SENSOR FOR DETECTING DAMAGE TO AN OBJECT

CROSS-REFERENCE TO RELATED APPLICATIONS

This application is a U.S. national stage filing under 35 U.S.C. §371 of International Application No. PCT/JP2012/002805, filed on Apr. 24, 2012, entitled "Sensor for Detecting Damage to an Object," the disclosure of which is incorporated by reference in its entirety.

TECHNICAL FIELD

The present disclosure relates generally to sensing techniques and, more particularly, to a sensor and method for detecting damage to an object.

BACKGROUND

Objects such as constructions or buildings are generally subject to arduous environments, and, as a result of this, are susceptible to various types of damage or degradation, such as corrosion, water leakage, or warpage/cracking. Such situations bring structurally serious damage to the objects, resulting in exorbitant repair costs. In such case, especially, where an internal state of the object cannot be visibly accessed, it would be difficult to detect the damage to the objects. Therefore, there is a need for detecting damage to the objects at an earlier stage. Further, a way to accurately indicate the situation wherein it is necessary to provide repair or replacement is required. In this case, establishing a sensing network system and connecting it to a monitoring system would lead to excessively high costs. Accordingly, providing an inexpensive and reliable system in order to broadly facilitate and practically implement such detection is required.

SUMMARY

In one aspect, the present disclosure sets forth a sensor for detecting damage to an object. The sensor may include a housing, a first coating provided on a surface of a first end of the housing, and a second coating provided on a surface of a second end of the housing opposing the first end. The first coating may be configured to be exposed to an environment in which the object is placed, while the second coating may be configured to be hermetically sealed. The sensor may further include a plurality of electrodes placed in the housing connected to the first end and the second end so as to measure an electrical signal generated therebetween.

In another aspect, a system for detecting damage to an object is provided. The system may include one or more sensors having a first coating on a first end of each housing of the sensors, a second coating hermetically sealed on a second end of the housing opposing the first end, and a plurality of electrodes placed in the housing connected to the first end and the second end to measure an electrical signal generated therebetween. The one or more sensors are placed in a part of a wall of the object and the first coating is configured to be exposed to an environment in which the object is placed. Further, at least one transmitter is operatively connected to the plurality of electrodes to transmit the electrical signals for analysis, and a computer is operatively connected to the transmitter to receive the electrical signals. The computer may be configured to analyze the electrical signals with reference data to detect the damage to the object.

In another aspect, a method for manufacturing a sensor is provided. The method may include providing a housing; placing a plurality of electrodes on a surface of the housing; applying a first coating on a first end of the housing; applying a second coating on a second end of the housing opposing the first end; and sealing the second coating hermetically.

In another aspect, a method for detecting damage to an object is provided. The method may include providing one or more sensor, and placing the one or more sensors in a part of a wall of an object. The one or more sensors may include a first coating on a first end of each housing of the one or more sensors, a second coating hermetically sealed on a second end of the housing opposing the first end, and a plurality of electrodes placed in the housing connected to the first end and the second end to measure an electrical signal generated therebetween. The method may further include measuring the electrical signals, and comparing the electrical signals to reference data.

DETAILED DESCRIPTION

In the following detailed description, reference is made to the accompanying drawings, which form a part hereof. In the drawings, similar symbols typically identify similar components, unless context dictates otherwise. Further, the drawings are intended to be explanatory and may not be drawn to scale. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure describes techniques, devices, apparatuses, systems, and methods for detecting damage to an object including, but not limited to, arranging at the object, a sensor, having two functional coatings, causing the sensor to output a detected signal to a computing device by comparing characteristics of the two functional coatings. The computing device may determine whether the object is damaged depending on the detected signal.

Figure 1:
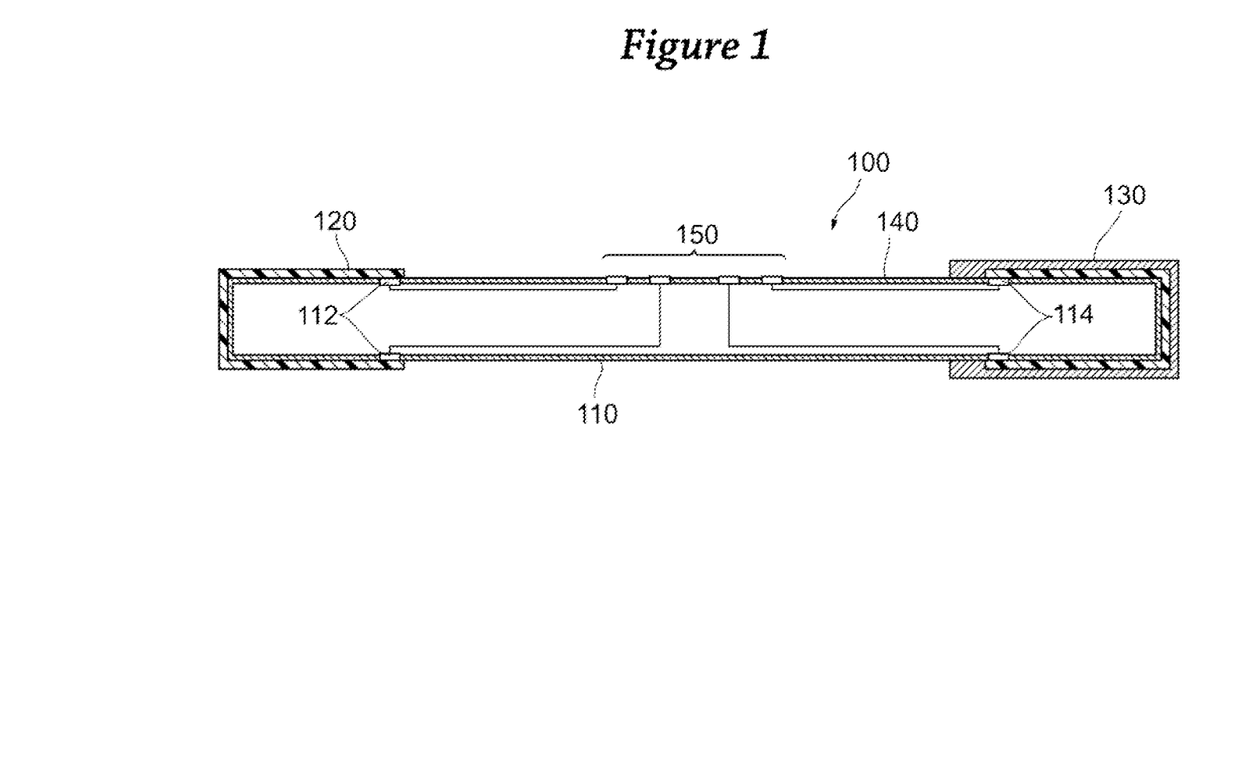
FIG. 1 is a schematic view of an example of a sensor arranged in accordance with the present disclosure.

FIG. 1 is a schematic cross-sectional view of a non-limiting example of a sensor arranged in accordance with the present disclosure. As shown in FIG. 1, the sensor 100 may include a housing 110 substantially defining the exterior thereof. The housing 110 may be formed in any shape, such as, but not limited to, a cylindrical shape or a plate-like shape. The housing 110 may be made of, but is not limited to being made of, a resin material, such as polyethylene, polycarbonate, or acrylonitrile butadiene styrene (ABS). As another non-limiting example, the housing 110 may be configured to be solid.

The sensor 100 may include, as functional coatings, a first coating 120 and a second coating 130. The first coating 120 may be arranged on a surface of a first end of the housing 110. In this non-limiting example, the first coating 120 may be arranged to cover a portion of a peripheral surface of the first end of the housing 110. The first coating 120 may have electrical characteristics, such as having a conductive property. The first coating 120 may be made of, for example, an ionic-conductive material or a polymethylmethacrylate (PMMA) resin material containing carbon nanotubes therein. As one non-limiting example, the ionic-conductive material may comprise an electrolyte comprising a lithium salt and polyethylene oxide. However, any material having electrical characteristics which change over time in the ambient air may be used. The first coating 120 may be electrically coupled to a pair of first electrodes 112 arranged on the surface of the first end of the housing 110.

The second coating 130 may be arranged to be sealed hermetically on a surface of a second end of the housing 110 opposing the first end. The second coating 130 may also be arranged to cover a portion of a peripheral surface of the second end of the housing 110. The second coating 130 may also have electrical characteristics which may change over time in the ambient air. The second coating 130 may be the same material as the first coating 120 but, alternatively, may be different from each other. The second coating 130 may also be electrically coupled to a pair of second electrodes 214 arranged on a surface of the housing 110.

The sensor 100 may include a cover 140 configured to hermitically seal the second coating 130. As one non-limiting example, the cover 140 may be attached to the housing 110 by way of thread fastening. As another non-limiting example, the cover 140 may be attached to a portion of the housing 110 by an adhesive. The cover 140 be made of, for example, but is not limited to being made of, the same material as that of the housing 110. Alternatively, the cover 140 may be made of, for example, glass or ceramic.

Further, the sensor 100 may include an interface 150 arranged on a surface of the housing 110. The interface 150 may include a plurality of terminals configured to be in mechanical and electrical contact with probes of a device (not shown) configured to measure an electrical signal flowing within the sensor 100.

Figure 2:
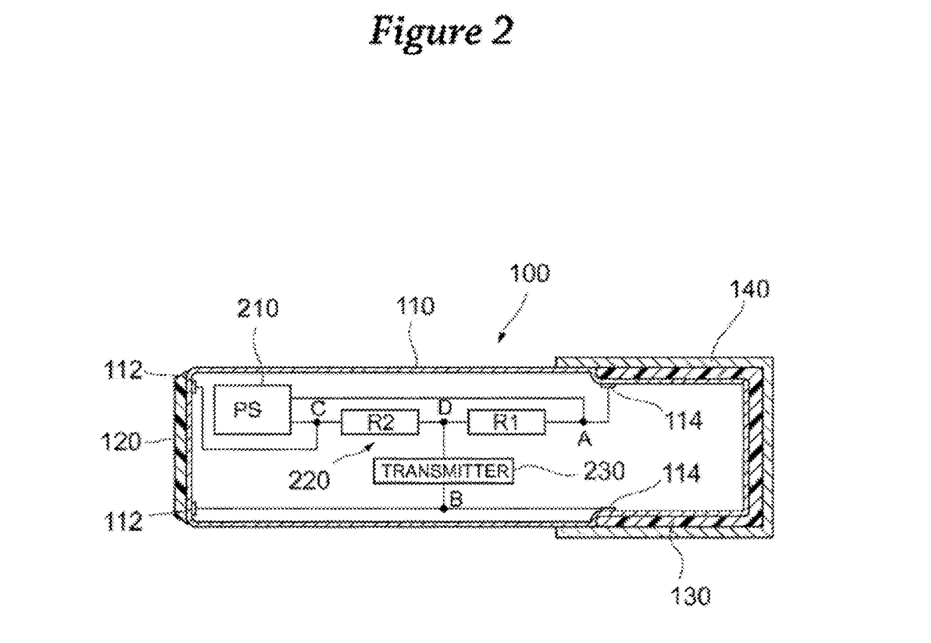
FIG. 2 is a schematic cross-sectional view of an example of a sensor arranged in accordance with the present disclosure.

FIG. 2 is a schematic cross-sectional view of a non-limiting example of a sensor arranged in accordance with the present disclosure. As shown in FIG. 2, the housing 110 of the sensor 100 may accommodate therein electrical components necessary to detect damage to an object. In this example, the sensor 100 may include a power supply circuit 210, a detection circuit 220, and a transmitter 230 in the housing 110.

As discussed above, the sensor 100 may include a first coating 120 and a second coating 130, each of which is arranged at the surface of each end of the housing 110. The first coating 120 may be electrically coupled to the circuitry in the housing via the first electrodes 112, whereas the second coating 130 may be electrically coupled to the circuitry via the second electrodes 114.

The power supply circuit 210 may include, but is not limited to, an antenna coil and a rectifier circuit (not shown). A reader 310 (see FIG. 3) being operatively close to the sensor 100, may allow the antenna coil to be induced by electromagnetic induction so as to produce an induction current. The induction current may be rectified by the rectifier circuit so as to be utilized as electric power for the detection circuit 220.

The detection circuit 220 may be configured to detect a change in the electrical characteristics of the first coating 120. As one non-limiting example, the detection circuit 220 may be configured to detect an electrical signal flowing between the first electrodes 112 and the second electrodes 114. In this example, the detection circuit 220 may include resistors R1 and R2 of known resistance, which are operatively coupled to the first coating 120 and the second coating 130, respectively, so that a Wheatstone bridge circuit can be composed.

Operation of the detection circuit 220 may be explained from the principle of the Wheatstone bridge circuit: Assuming that the resistance of the first coating 120 is defined as being Rx, of unknown resistance, and the resistance of the second coating is defined as being R3, of known resistance, if the ratio of the two resistances in a known leg (R2/R1) is equal to the ratio of the two resistances in an unknown leg (Rx/R3), then the voltage between the two midpoints (B and D) will be zero and no current will flow through the transmitter 230. If the bridge is unbalanced, the direction of the current indicates whether Rx is too high or too low.

Accordingly, the bridge of the detection circuit 220 may be adjusted to be balanced at the initial state. After that, upon operation of the detection circuit 220, if the bridge is unbalanced due to a change in the resistance caused by a deterioration of the first coating 120, the bridge may allow a current to flow through the transmitter 230.

The transmitter 230 is configured to transmit an electrical signal to the reader 310 if there exists the current flowing through the transmitter 230. One non-limiting example of the transmitter 230 may be a passive RFID transmitter.

Figure 3:
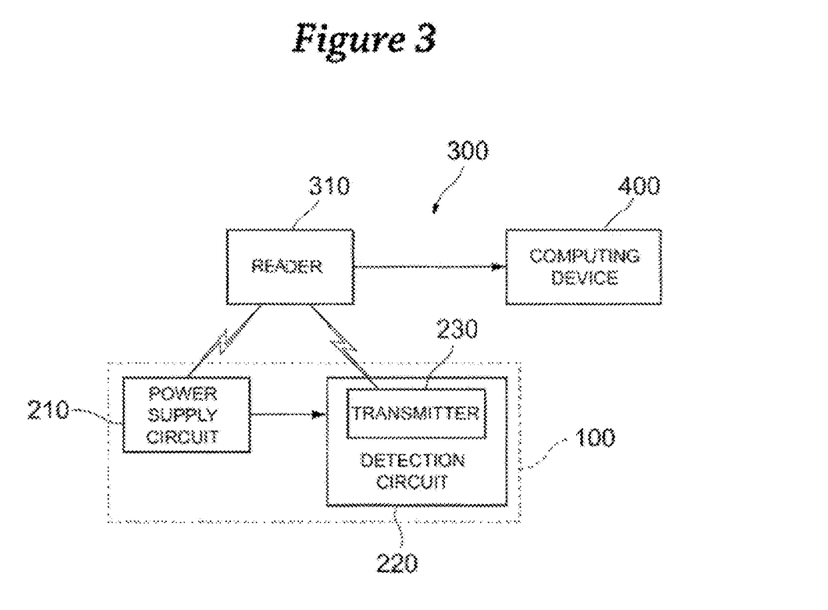
FIG. 3 is a block diagram of an example of a system including a sensor arranged in accordance with the present disclosure.

FIG. 3 is a block diagram of a non-limiting example of a system, including a sensor, arranged in accordance with the present disclosure. Referring to FIG. 3, a system 300 may be configured to include the sensor 100, the reader 310 and a computing device 400. Although, in this example, the detection circuit 220 may be arranged within the sensor 100, it may alternatively be arranged independently, outside of the sensor 100.

The sensor 100 may be configured to allow wireless communication with the reader 310. Specifically, when the reader 310, which may irradiate a radio wave for power, approaches the sensor 100, the antenna coil (not shown) of the power supply circuit 210 may be induced by electromagnetic induction, so that an induction current can be produced. The rectifier circuit (not shown) of the power supply circuit 210 may then rectify the induction current so as to allow it to be utilized as electrical power for the detection circuit 220, and thus, the detection circuit 220 may be driven by the electrical power. The detection circuit 220 may be configured to detect a change in the electrical characteristics of the first coating 120. Further, the detection circuit 220 may include the transmitter 230. Thus, the detection circuit 220 may allow the transmitter 230 to transmit an electrical signal caused by a current to flow through the first electrodes 112 and the second electrodes 114. As discussed above, the detection circuit 22 may include a Wheatstone bridge circuit in which each of the first coating 120 and the second coating 130 respectively function as ones of the resistors. If the resistance of the first coating 120 changes over time, the bridge may be unbalanced and thus allow the current to flow through the transmitter 230. As a result of this, the transmitter 230 may transmit an electrical signal to the reader 310 based on the current. The reader 310 may receive the electrical signal from the transmitter 260, and then transfer it to the computing device 400 for analysis.

Figure 4:
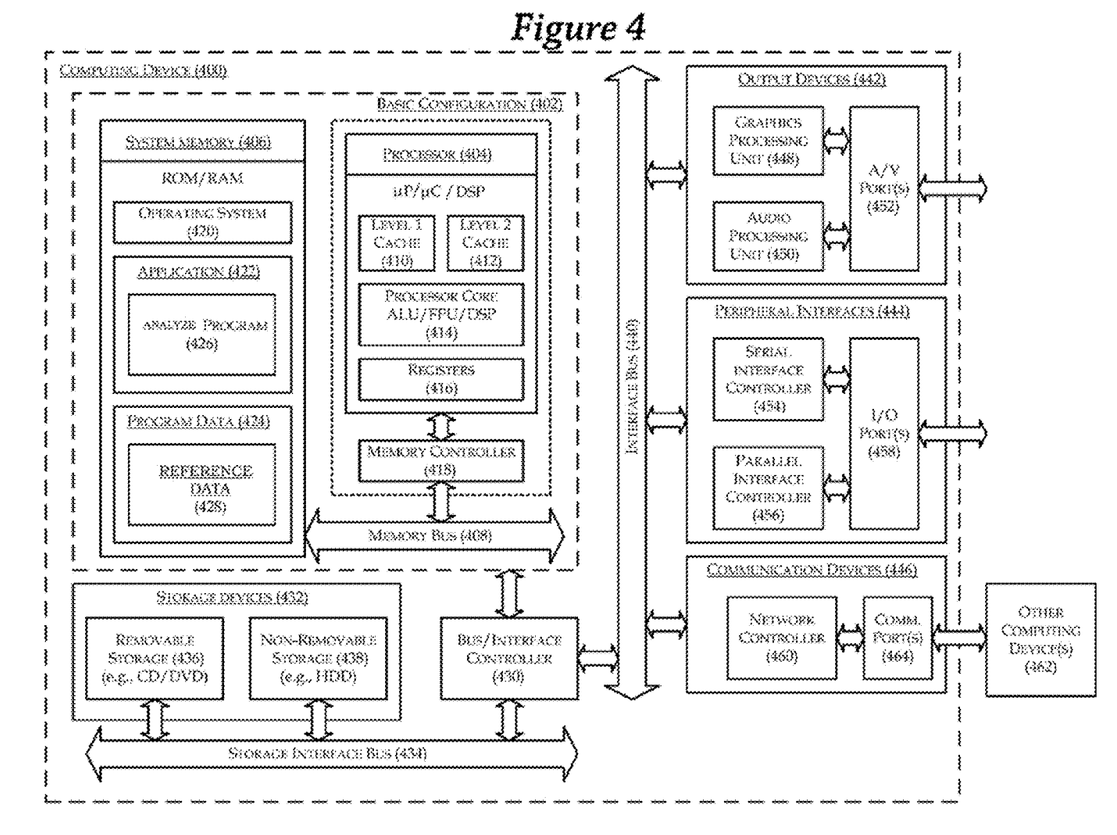
FIG. 4 is a block diagram illustrating an example of a computing device that is arranged for a system including a sensor for detecting damage to an object in accordance with the present disclosure.

FIG. 4 is a block diagram illustrating a non-limiting example of a computing device 400 that is arranged for a system including a sensor for detecting damage to an object in accordance with the present disclosure. In a very basic configuration 402, the computing device 400 may typically include one or more processors 404 and a system memory 406. A memory bus 408 may be used for communicating between a processor 404 and a system memory 406.

Depending on the desired configuration, the processor 404 may be of any type, including but not limited to a microprocessor, a microcontroller, a digital signal processor (DSP), or any combination thereof. The processor 404 may include one more levels of caching, such as a level one cache 410 and a level two cache 412, a processor core 414, and registers 416. A non-limiting example of a processor core 414 may include an arithmetic logic unit (ALU), a floating point unit (FPU), a digital signal processing core (DSP Core), or any combination thereof. An example memory controller 418 may also be used with the processor 404, or in some implementations a memory controller 418 may be an internal part of the processor 404.

Depending on the desired configuration, the system memory 406 may be of any type, including but not limited to, volatile memory (such as RAM), non-volatile memory (such as ROM, flash memory, etc.) or any combination thereof. The system memory 406 may include an operating system 420, one or more applications 422, and program data 424. The application 422 may include an analyzing program 426 that is arranged to analyze the electrical signal obtained from the sensor 100. The program data 424 may include reference data 428 that may be retrieved from the sensor at the initial state described herein. In some embodiments, the application 422 may be arranged to operate with the program data 424 on the operating system 420 such that the analysis can be performed. In a process of the analysis, the obtained electrical signal may be compared to the reference data 428. This above-described basic configuration 402 is illustrated in FIG. 4 by those components within the innermost dashed line.

The computing device 400 may have additional features or functionality, and additional interfaces to facilitate communications between the basic configuration 402 and any required devices and interfaces. For example, a bus/interface controller 430 may be used to facilitate communications between the basic configuration 402 and one or more data storage devices 432 via a storage interface bus 434. The data storage devices 432 may be removable storage devices 436, non-removable storage devices 438, or a combination thereof. Non-limiting examples of removable storage and non-removable storage devices may include magnetic disk devices, such as flexible disk drives and hard-disk drives (HDD), optical disk drives such as compact disk (CD) drives or digital versatile disk (DVD) drives, solid state drives (SSD), and tape drives, to name a few. Non-limiting examples of the computer storage media may include volatile and non-volatile, removable and non-removable media implemented in any method or technology for the storage of information, such as computer readable instructions, data structures, program modules, or other data.

The system memory 406, removable storage devices 436 and non-removable storage devices 438 are non-limiting examples of computer storage media. The computer storage media may include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by the computing device 400. Any such computer storage media may be part of the computing device 400.

The computing device 400 may also include an interface bus 440 for facilitating communication from various interface devices (e.g., output devices 442, peripheral interfaces 444, and communication devices 446) to the basic configuration 402 via the bus/interface controller 430. Non-limiting examples of the output devices 442 include a graphics processing unit 448 and an audio processing unit 450, which may be configured to communicate to various external devices, such as a display or speakers via one or more A/V ports 452. Non-limiting examples of the peripheral interfaces 444 include a serial interface controller 454 or a parallel interface controller 456, which may be configured to communicate with external devices such as input devices (e.g., keyboard, mouse, stylus, voice input device, touch input device, etc.) or other peripheral devices (e.g., printer, scanner, etc.) via one or more I/O ports 458. A non-limiting example of a communication device 446 includes a network controller 460, which may be arranged to facilitate communications with one or more other computing devices 462 over a network communication link via one or more communication ports 464.

The network communication link may be one non-limiting example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 400 may be implemented as a portion of a small-form factor portable (or mobile) electronic device, such as a cell phone, a personal data assistant (PDA), a personal media player device, a wireless web-watch device, a personal headset device, an application specific device, or a hybrid device that includes any of the above functions. The computing device 400 may also be implemented as a personal computer, including both laptop computer and non-laptop computer configurations.

Figure 5:
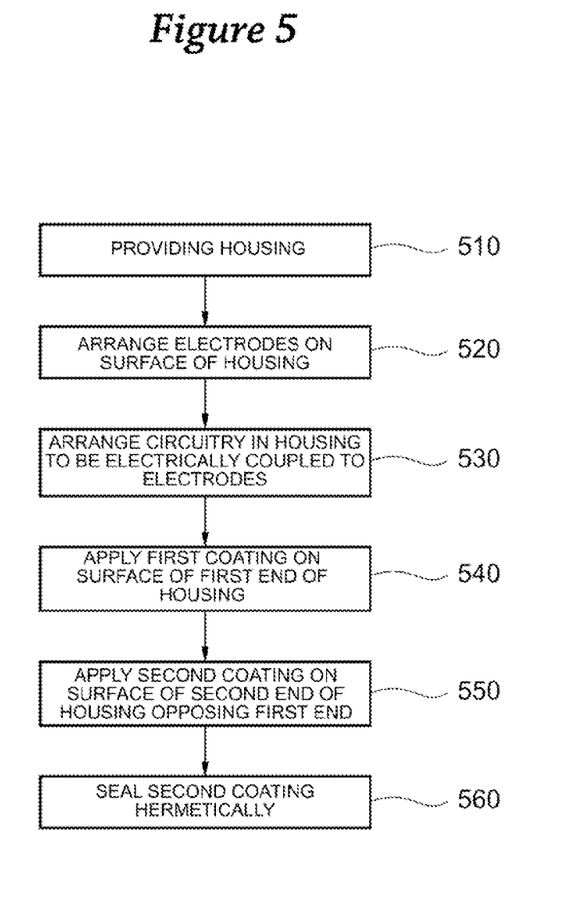
FIG. 5 is a flow chart of an example of a method of manufacturing a sensor arranged in accordance with the present disclosure.

FIG. 5 is a flow chart of a non-limiting example of a method of manufacturing a sensor arranged in accordance with the present disclosure.

Referring to FIG. 5, in an operation 510, the housing 110 may be formed in a desired shape. As one non-limiting example, the housing 110 may be in a plate-like shape. In an operation 520, the plurality of electrodes may be arranged at predetermined positions on the surface of the housing 110. As a further non-limiting example, the first electrodes 112 may be arranged on the surface of the first end of the housing 110, whereas the second electrodes 114 may be arranged on the surface of the second end of the housing opposing the first end. In an operation 530, the circuitry for detecting an electrical signal may be arranged in the housing 110. Electrical wiring of the circuitry may electrically be coupled to the first electrodes 112 and the second electrodes 114. In an operation 540, the first coating 120 may be applied on the surface of the first end of the housing 110. The first coating 120 may be formed on the surface by a dipping process. The thickness of the first coating 120 may be adjusted depending on a desired electrical resistance. In the operation 550, the second coating 130 may be applied on the surface of the first end of the housing 110 in the same or similar manner to that of the first coating 120, described above. In an operation 560, the second coating 130 may be hermitically sealed. As a further non-limiting example, the second coating 130 may be covered by attaching the cover 140. Alternatively, a sealing material, such as glass or ceramic may be applied onto the entire second coating 130 to be hermitically sealed. By this way, the aforementioned sensor 100 may be obtained.

Figure 6:
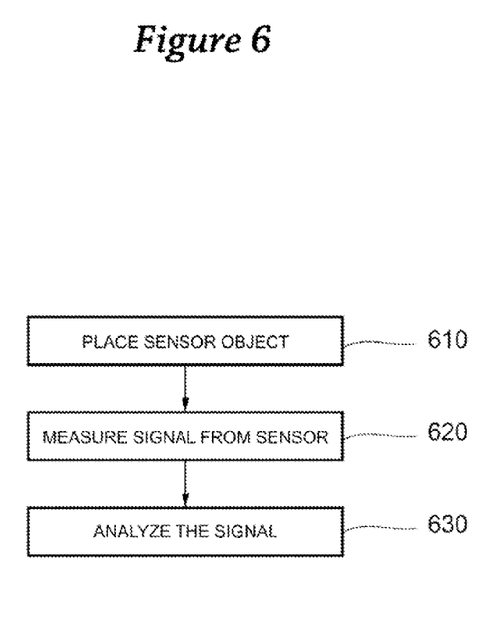
FIG. 6 is a flow chart of an example of a method of detecting damage to an object arranged in accordance with the present disclosure.

FIG. 6 is a flow chart of a non-limiting example of a method of detecting damage to an object arranged in accordance with the present disclosure.

Referring to FIG. 6, in an operation 610, the sensor 100 may be placed in an object which is intended to detect damage due to the passage of time so that the first coating 120 of the sensor 100 may be exposed to an environment in which the object is placed. In an operation 620, an electrical signal from the sensor may be measured and read out. As one non-limiting example, the reader 310 may be used to measure the electrical signal. Namely, upon approaching the reader 310, the electrical power may be supplied to the detection circuit 220 of the sensor 100, and if the electrical characteristics of the first coating 120 change, the transmitter 230 may transmit the electrical signal depending on the electrical characteristics to the reader 310. The reader 310 may receive the electrical signal from the sensor 100, and then transfer it to the computing device 400. In an operation 630, the computing device 400 may analyze the electrical signal to determine whether the object has been damaged.

Figure 7:
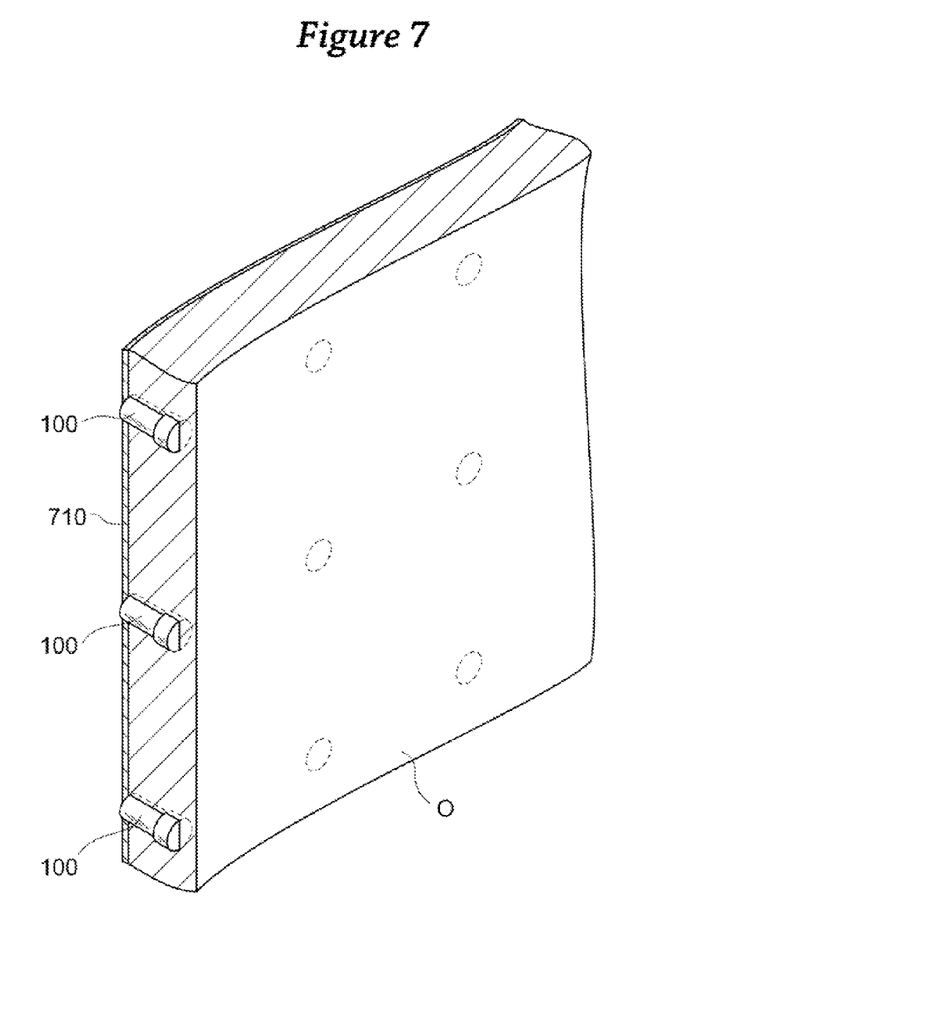
FIG. 7 is a schematic view of an example of a sensor in use arranged in accordance with the present disclosure.

FIG. 7 is a schematic view of a non-limiting example of a sensor in use arranged in accordance with the present disclosure. Referring to FIG. 7, a plurality of sensors 100 may be embedded in a wall or partition of an object O, such as, but not limited to, a construction, container, or package. The wall may be perforated to receive each of the plurality of sensors 100. Although the plurality of sensors 100 are shown in FIG. 7, an individual sensor 100 may be employed for the object O. The number of sensors 100 may be selected to a large extent depending on the size of the object O. The plurality of sensors 100 may be placed in a grid at a predetermined distance.

The object O may include a functional coating 710 arranged on a surface of the wall thereof. It would be understood that the functional coating 710 may be exposed to an environment in which the object is placed. A portion of the functional coating 710 may serve as a part of the sensor 100, such portion is herein referred to as the first coating 120. After a long time has passed since the application of the functional coating 710, the electrical signal from the sensor 100 may be measured.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

While the present disclosure has been described with respect to a limited number of embodiments, those skilled in the art, having the benefit of this disclosure, will appreciate that other embodiments can be devised which do not depart from the scope of the present disclosure as disclosed herein. Accordingly, the scope of the present disclosure should be limited only by the attached claims.

The invention claimed is:

1. A sensor for detecting damage to an object, the sensor comprising:
    a housing;
    a first coating provided on a surface of a first end of the housing and configured to be exposed to an environment in which the object is placed;
    a second coating hermetically sealed and provided on a surface of a second end of the housing opposing the first end; and
    a plurality of electrodes placed in the housing and electrically connected to the first coating and the second coating, the plurality of electrodes configured to measure an electrical signal generated between the first coating and the second coating, wherein the electrical signal is indicative of a change in an electrical characteristic of the first coating as compared to the second coating.

2. The sensor of claim 1, wherein the first coating is made of an ionic-conductive material, and the second coating is made of an ionic-conductive material.

3. The sensor of claim 2, wherein the first coating and the second coating are made of the same material.

4. The sensor of claim 2, wherein the ionic-conductive material used to make each of the first coating and the second coating comprises an electrolyte comprising a lithium salt and polyethylene oxide.

5. The sensor of claim 1, wherein the first coating and the second coating comprise a polymethylmethacrylate (PMMA) resin containing carbon nanotubes therein.

6. The sensor of claim 1, further comprising a cover arranged at the second end and configured to hermetically seal the second coating.

7. The sensor of claim 1, further comprising a Wheatstone bridge circuit electrically connected to the plurality of electrodes.

8. The sensor of claim 1, further comprising a transmitter configured to transmit the electrical signal for analysis.

9. The sensor of claim 8, wherein the transmitter is a passive RFID transmitter.

10. A system for detecting damage to an object, the system comprising:
    one or more sensors having a first coating on a first end of each housing of the sensors, a second coating hermetically sealed on a second end of the housing opposing the first end, and a plurality of electrodes placed in the housing and electrically connected to the first coating and the second coating, the plurality of electrodes configured to measure an electrical signal generated between the first coating and the second coating, wherein the electrical signal is indicative of a change in an electrical characteristic of the first coating as compared to the second coating,
    wherein the one or more sensors are placed in a part of a wall of the object and the first coating is configured to be exposed to an environment in which the object is placed,
    wherein at least one transmitter is operatively connected to the plurality of electrodes to transmit the electrical signals for analysis, and
    wherein a computer is operatively connected to the transmitter to receive the electrical signals and configured to analyze the electrical signals with reference data to detect the damage to the object.

11. The system of claim 10, wherein the first coating is made of an ionic-conductive material, and the second coating is made of an ionic-conductive material.

12. The system of claim 11, wherein the first coating and the second coating are made of the same material.

13. The system of claim 11, wherein the ionic-conductive material used to make each of the first coating and the second coating comprises an electrolyte comprising a lithium salt and polyethylene oxide.

14. The system of claim 11, wherein the first coating and the second coating of each of the one or more sensors comprise a polymethylmethacrylate (PMMA) resin containing carbon nanotubes therein.

15. The system of claim 10, wherein each of the one or more sensors includes a Wheatstone bridge circuit electrically connected to the plurality of electrodes.

16. The system of claim 10, wherein the one or more sensors are placed in a grid.

17. The system of claim 10, wherein each of the one or more sensors includes a memory to store an identifier, wherein the computer manages placement information assigned to each of the identifiers, the placement information indicating where each sensor is placed in the wall.

18. The system of claim 10, wherein the at least one transmitter is a passive RFID transmitter.

19. The system of claim 10, wherein the object is at least one selected from the group consisting of a construction, a container, and a package.

20. A method for manufacturing a sensor, the method comprising:
   providing a housing;
   placing a plurality of electrodes on a surface of the housing;
   applying a first coating on a first end of the housing such that at least a first portion of the plurality of electrodes are electrically connected to the first coating;
   applying a second coating on a second end of the housing opposing the first end such that at least a second portion of the plurality of electrodes are electrically connected to the second coating; and
   sealing the second coating hermetically,
   wherein the plurality of electrodes are configured to measure an electrical signal generated between the first coating and the second coating, and
   wherein the electrical signal is indicative of a change to an electrical characteristic of the first coating as compared to the second coating.

21. The method of claim 20, further comprising connecting a transmitter to the plurality of electrodes, the transmitter being configured to transmit the electrical signal generated therebetween.

22. The method of claim 20, wherein the sealing of the second coating includes attaching a cover to the second end of the housing.

23. A method for detecting damage to an object, the method comprising:
   providing one or more sensors having a first coating on a first end of each housing of the one or more sensors configured to be exposed to an environment in which the object is exposed, a second coating hermetically sealed on a second end of the housing opposing the first end, and a plurality of electrodes placed in the housing and electrically connected to the first coating and the second coating to measure an electrical signal generated between the first coating and the second coating, wherein the electrical signal is indicative of a change to an electrical characteristic of the first coating as compared to the second coating;
   placing the one or more sensors in a part of a wall of the object;
   measuring the electrical signals; and
   comparing the electrical signals to reference data.

24. The method of claim 23, further comprising transmitting the measured electrical signals to a computer, wherein the computer performs the comparison for analysis.

25. The method of claim 23, further comprising identifying a position at which the object is damaged based on results of the comparison.

26. The method of claim 23, wherein the object is at least one selected from the group consisting of a construction, a container, and a package.

* * * * *